United States Patent [19]
Sharifi et al.

[11] Patent Number: 6,124,260
[45] Date of Patent: Sep. 26, 2000

[54] INHIBITION OF SMOOTH MUSCLE CELL MIGRATION BY TENASCIN-C PEPTIDES

[75] Inventors: Behrooz G. Sharifi, Woodland Hills; Prediman K. Shah, Los Angeles, both of Calif.

[73] Assignee: Cedars-Sinai Medical Center, Los Angeles, Calif.

[21] Appl. No.: 09/164,021

[22] Filed: Sep. 30, 1998

[51] Int. Cl.$^7$ .................................................. A61K 38/00
[52] U.S. Cl. ........................... 514/12; 530/324; 530/395; 424/185.1; 514/8
[58] Field of Search .................................... 530/324, 395, 530/300, 350; 514/885, 2, 8, 12; 424/185.1

[56] References Cited

U.S. PATENT DOCUMENTS

| | | |
|---|---|---|
| 5,092,885 | 3/1992 | Yamada et al. . |
| 5,169,930 | 12/1992 | Ruoslahti et al. . |
| 5,246,451 | 9/1993 | Trescony et al. . |
| 5,512,474 | 4/1996 | Clapper et al. . |
| 5,622,975 | 4/1997 | Singh et al. . |
| 5,674,848 | 10/1997 | Bhatnagar . |
| 5,681,931 | 10/1997 | Reid et al. . |
| 5,684,133 | 11/1997 | Schwab et al. . |
| 5,710,159 | 1/1998 | Voss et al. . |

FOREIGN PATENT DOCUMENTS

94/21664  9/1994  WIPO ......................................... 21/4

OTHER PUBLICATIONS

LaFleur et al.;Aortic Smooth Muscle Cells Interact with Tenascin–C through its Fibrinogen–like Domain; FASEB Journal 12(4) pA479, Mar., 17, 1998.

Joshi et al.; Endothelial cells adhere to the RGD domain and the Fibrinogen–like terminal knob of tenascin; J. Cell Sci. 106 (pt 1); 389–400, 1993.

Chiquet et al.; Isolation of chick tenascin fvariants and fragments (A C–terminal heparin–binding fragment produced by cleavage of the extra domain from the largest subunit splicing variant); Eur. J. Biochem.; 199; 379–388, 1991.

Majesky et al.; Neointima Formation after Acute Vascular Injury; Texas Heart Inst. J. 21 (1) 78–85, 1994.

Wehrle–Haller et al.; J. of Cell Sci.; 106; 597–610, 1993.

David W. LaFleur et al., "Aortic Smooth Muscle Cells Interact with Tenascin–C through its Fibrinogen–like Domain," *The Journal of Biological Chemistry*, vol. 272, No. 52, pp. 32798–32803, 1997.

Gordon A.A. Ferns et al., "Inhibition of Neointimal Smooth Muscle Accumulation after Angioplasty by an Antibody to PDGF," *Science*, vol. 253, No. 5024, pp. 1129–1132, 1991.

Eric T. Choi, et al., "Inhibition of neointimal hyperplasia by blocking $\alpha_v\beta_3$ integrin with a small peptide antagonist GpenGRGDSPCA," *Journal of Vascular Surgery*, vol. 19, No. 1, pp. 125–134, 1994.

Daniel Kirchhofer et al., "$\alpha_2\beta_1$ Integrins from Different Cell Types Show Different Binding Specificities," *The Journal of Biological Chemistry*, vol. 265, No. 2, pp. 615–618, 1990.

Aarno Hautanen et al., "Effects of Modifications of the RGD Sequence and Its Context on Recognition by the Fibronectin Receptor," *The Journal of Biological Chemistry*, vol. 264, No. 3, pp. 1437–1442, 1989.

Mario A. Bourdon et al., "Tenascin Mediates Cell Attachment through an RGD–dependent Receptor," *The Journal of Cell Biology*, vol. 108, pp. 1149–1155, Mar. 1989.

P. Sriramarao et al., "Endothelial Cell attachment and spreading on human tenascin is mediated by $\alpha_2\beta_1$ and $\alpha_v\beta_3$ integrins," *Journal of Cell Science*, 105, pp. 1001–1012, 1993.

Enno Aufderheide et al., "Tenascin During Gut Development: Appearance in the Mesenchyme, Shift in Moledular Forms, and Dependence on Epithelial–Mesenchymal Interactions," *The Journal of Cell Biology*, vol. 107, No. 6, 2341–2349, 1988.

Paritosh Joshi et al., "Endothelial cells adhere to the RGD domain and the fibrinogen–like terminal knob of tenascin," *Journal of Cell Science*, 106, pp. 389–400, 1993.

Harold P. Erickson et al., "Tenascin: an Extracellular Matrix Protein Prominent in Specialized Embryonic Tissues and Tumors," *Annu. Rev. Cell Biol.*, 1989 5:71–92.

Ikramuddin Aukhil et al., "Cell– and Heparin–binding Domains of the Hexabrachion Arm Identified by Tenascin Expression Proteins," *Journal of Biological Chemistry*, vol. 268, No. 4, pp. 2542–2553, 1993.

*Primary Examiner*—Christina Y. Chan
*Assistant Examiner*—Patrick J. Nolan
*Attorney, Agent, or Firm*—Loeb & Loeb LLP

[57] ABSTRACT

Peptides capable of interacting with smooth muscle cells are provided. Peptides are derived from Tenascin-C protein, particularly from the Fbg-L domain of Tenascin-C protein. Peptides of the present invention are useful in inhibiting smooth muscle cell migration. Methods of inhibiting smooth muscle cell adhesion and migration are also provided. Methods of the present invention may be used for treating intimal hyperplasia, restenosis, and atherosclerosis.

8 Claims, 9 Drawing Sheets

[I]    MIGLLYPFPKDCSQAMLNGDTTSGLYTIYL

[II]   YTIYLNGDKAQALEVFCDMTSDGGGWIVFL

[III]  WIVFLRRKNGRENFYQNWKAYAAGFGDRRE

[IV]   GDRREEFLHWLGLDNLNKITAQGQYELRVD

[V]    ELRVDLRDHGETAFAVYDKFSVGDAKTRYK

[VI]   KTRYKLKVEGYSGTAGDSMAYHNGRSFST

[VII]  RSFSTFDKDTDSAITNCALSYKGAFWYRNC

[VIII] WYRNCHRVNLMGRYGDNNHSQGVNWFHWKG

[IX]   FHWKGHEHSIQFAEMKLRPSNFRNLEGRRKRA

Fig. 7

SEQUENCE LISTING

```
<160> NUMBER OF SEQ ID NOS: 11

<210> SEQ ID NO 1
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide sequence

<400> SEQUENCE: 1

Met Ile Gly Leu Leu Tyr Pro Phe Pro Lys Asp Cys Ser Gln Ala Met
 1               5                  10                  15

Leu Asn Gly Asp Thr Thr Ser Gly Leu Tyr Thr Ile Tyr Leu
            20                  25                  30

<210> SEQ ID NO 2
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide sequence

<400> SEQUENCE: 2

Tyr Thr Ile Tyr Leu Asn Gly Asp Lys Ala Gln Ala Leu Glu Val Phe
 1               5                  10                  15

Cys Asp Met Thr Ser Asp Gly Gly Gly Trp Ile Val Phe Leu
            20                  25                  30

<210> SEQ ID NO 3
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide sequence

<400> SEQUENCE: 3

Trp Ile Val Phe Leu Arg Arg Lys Asn Gly Arg Glu Asn Phe Tyr Gln
 1               5                  10                  15

Asn Trp Lys Ala Tyr Ala Ala Gly Phe Gly Asp Arg Arg Glu
            20                  25                  30
```

<210> SEQ ID NO 4
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide sequence

<400> SEQUENCE: 4

Gly Asp Arg Arg Glu Glu Phe Leu His Trp Leu Gly Leu Asp Asn Leu
 1               5                  10                  15

Asn Lys Ile Thr Ala Gln Gly Gln Tyr Glu Leu Arg Val Asp
            20                  25                  30

<210> SEQ ID NO 5
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide sequence

<400> SEQUENCE: 5

Glu Leu Arg Val Asp Leu Arg Asp His Gly Glu Thr Ala Phe Ala Val
 1               5                  10                  15

Tyr Asp Lys Phe Ser Val Gly Asp Ala Lys Thr Arg Tyr Lys
            20                  25                  30

<210> SEQ ID NO 6
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide sequence

<400> SEQUENCE: 6

Lys Thr Arg Tyr Lys Leu Lys Val Glu Gly Tyr Ser Gly Thr Ala Gly
 1               5                  10                  15

Asp Ser Met Ala Tyr His Asn Gly Arg Ser Phe Ser Thr
            20                  25

<210> SEQ ID NO 7
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide sequence

<400> SEQUENCE: 7

Arg Ser Phe Ser Thr Phe Asp Lys Asp Thr Asp Ser Ala Ile Thr Asn
 1               5                  10                  15

Cys Ala Leu Ser Tyr Lys Gly Ala Phe Trp Tyr Arg Asn Cys
            20                  25                  30

<210> SEQ ID NO 8
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide sequence

<400> SEQUENCE: 8

```
-continued

Trp Tyr Arg Asn Cys His Arg Val Asn Leu Met Gly Arg Tyr Gly Asp
 1               5                  10                  15

Asn Asn His Ser Gln Gly Val Asn Trp Phe His Trp Lys Gly
            20                  25                  30

<210> SEQ ID NO 9
<211> LENGTH: 32
<212> TYPE: PRT
<213> ORGANISM: Artificial Sequence
<220> FEATURE:
<223> OTHER INFORMATION: Description of Artificial Sequence: Synthetic
      peptide sequence

<400> SEQUENCE: 9

Phe His Trp Lys Gly His Glu His Ser Ile Gln Phe Ala Glu Met Lys
 1               5                  10                  15

Leu Arg Pro Ser Asn Phe Arg Asn Leu Glu Gly Arg Arg Lys Arg Ala
            20                  25                  30

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide sequence

<400> SEQUENCE: 10

Gly Arg Gly Asp Ser
 1               5

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide sequence

<400> SEQUENCE: 11

Gly Arg Phe Asp Ser
 1               5
```

INHIBITION OF SMOOTH MUSCLE CELL MIGRATION BY TENASCIN-C PEPTIDES

BACKGROUND OF THE INVENTION

1. Area of the Art

The invention relates generally to the regulation of cell movement and specifically to the inhibition of smooth muscle cell (SMC) movement by Tenascin-C peptides.

2. Description of the Prior Art

Throughout this application, various references are referred to within parentheses. Disclosures of these publications in their entireties are hereby incorporated by reference into this application to more fully describe the state of the art to which this invention pertains. Full bibliographic citation for these references may be found at the end of this application, preceding the claims.

Neointima formation is a leading cause of the pathogenesis of vascular diseases such as atherosclerosis, restenosis following percutaneous transluminal coronary angioplasty (PTCA), and vein bypass atherosclerosis. Migration of vascular smooth muscle cells from media to intima plays a critical role in neointima formation (1–3). After surgical injury to the arterial integrity, activated smooth muscle cells migrate and then proliferate in the neointima (4). Accumulation of SMCs and deposition of an extracellular matrix lead to a hemodynamically compromising neointimal lesion, which is developed in a fraction of the time that is needed for the development of the primary atherosclerotic lesion (5). To prevent intimal hyperplasia, restenosis and atherosclerosis, the rapid accumulation of SMCs in the neointima must be inhibited (6).

Excessive SMC proliferation and migration occur as a result of growth factors produced by cellular constituents in the blood and the damaged arterial vessel wall which mediates the proliferation of SMCs in vascular restenosis. SMC migration may be activated by chemotactic agents, such as PDGF-BB and angiotensin II, and chemokinetic agents such as PDGF. Antibodies to growth factor PDGF may inhibit neointimal smooth muscle cell accumulation after angioplasty (6).

The SMC migration is mediated by interaction of SMC surface receptors and the extracellular matrix. The process of cell attachment to the matrix is frequently mediated by a family of cell-surface receptors called integrins (7). These receptors constitute a family of proteins with share structural characteristics of noncovalent, heterodimeric glycoprotein complexes including $\alpha$ and $\beta$ subunits. Integrin receptors are believed to form a link between the extracellular and intracellular environments and to affect cellular behavior by transmitting extracelluar signals to the intracellular compartment.

Some integrins recognize and bind to specific amino acid sequences within matrix macromolecules. For example, the integrin receptors on a number of cell types recognize an arginine-glycine-aspartic acid sequence (RGD) within the cell-binding domain of the extracelluar matrix proteins (8). The smooth muscle cell has at least six of these RGD-dependent integrins, including the fibronectin receptor $\alpha_5\beta_1$, the vitronectin receptor $\alpha_v\beta_3$, and the platelet glycoprotein IIb/IIIa, $\alpha_{IIb}\beta_{IIIa}$. Peptides that block integrin $\alpha_v\beta_3$ can inhibit neointimal hyperplasia (9).

It has been observed that chemotactic factors, including PDGF-BB and angiotensin II, markedly induce Tenascin-C gene expression in SMCs (10, 11). Tenascin-C is an oligomeric glycoprotein composed of multiple domains that has been implicated in cell migration (12–18). Human, mouse, and chicken Tenascin-C contain a cysteine-rich segment at their amino termini through which the six Tenascin-C monomers link into a hexamer. This segment is followed by epidermal growth factor-like repeats, fibronectin-type III repeats (FN-L) and a globular carboxyl terminus, homologous to fibrinogen (Fbg-L) (19). These domains mediate the interaction between the Tenascin-C molecule and cells. For example, endothelial cells interact with Tenascin-C through its fibrinogen-like domain (20), whereas the FN-L domain of Tenascin-C mediates interaction with fibroblast (21).

However, the interaction of SMCs with Tenascin-C is unknown. Particularly, the specific domain of Tenascin-C that mediates its interaction with SMCs is unknown. It is desirable to study the molecular mechanism of Tenascin-C-SMC interactions, and therefore to provide agents that inhibit the migration of smooth muscle cells that are useful in the treatment and prevention of intimal hyperplasia, restenosis and atherosclerosis.

SUMMARY OF THE INVENTION

It is an object of the present invention to study the interaction of Tenascin-C with smooth muscle cells, and therefore to provide novel factors to regulate smooth muscle cell migration, and methods thereof.

One aspect of the present invention provides synthetic peptides derived from a Tenascin-C protein, wherein the polypeptides are capable of interacting with smooth muscle cells. In one Embodiment of the present invention, the peptides are derived from the Fbg-L domain of the Tenascin-C protein.

Another aspect of the present invention provides a method of inhibiting the Tenascin-C protein mediated smooth muscle cell adhesion and migration. A method in accordance with the present invention comprises contacting the SMC with an effective amount of a factor capable of reducing the interaction of the SMC with the Tenascin-C protein. In one embodiment of the present invention, the factor is a peptide of the present invention. In another embodiment of the present invention, the factor is EDTA. In yet another embodiment of the present invention, the factor is an antibody against the Tenascin-C protein.

A further aspect of the present invention provides a method of inhibiting Tenascin-C mediated vascular smooth muscle cell adhesion and migration in a host. A method in accordance with the present invention comprises administering to the host in need of the inhibition an effective amount of a factor capable of reducing the interaction of the SMC with the Tenascin-C protein. In accordance with the present invention, the factor can be a peptide or an antibody of the present invention.

Yet another aspect of the present invention provides a pharmaceutical composition comprising a therapeutically effective amount of a factor capable of reducing the interaction of the SMC with the Tenascin-C protein, and a pharmaceutically acceptable carrier. In accordance with embodiments of the present invention, the factor can be a peptide or an antibody of the present invention.

The invention is defined in its fullest scope in the appended claims and is described below in its preferred embodiments.

DESCRIPTION OF THE FIGURES

The above-mentioned and other features of this invention and the manner of obtaining them will become more apparent, and will be best understood by reference to the following description, taken in conjunction with the accompanying drawings. These drawings depict only a typical embodiment of the invention and do not therefore limit its scope. They serve to add specificity and detail, in which:

FIG. 7 shows amino acid sequences of peptide I through IX representing the N-terminal through C-terminal part of the Fbg-L domain, SEQ ID NOS. 1–9. The overlapping sequences have been underlined.

DETAILED DESCRIPTION OF THE INVENTION

Figure 1:
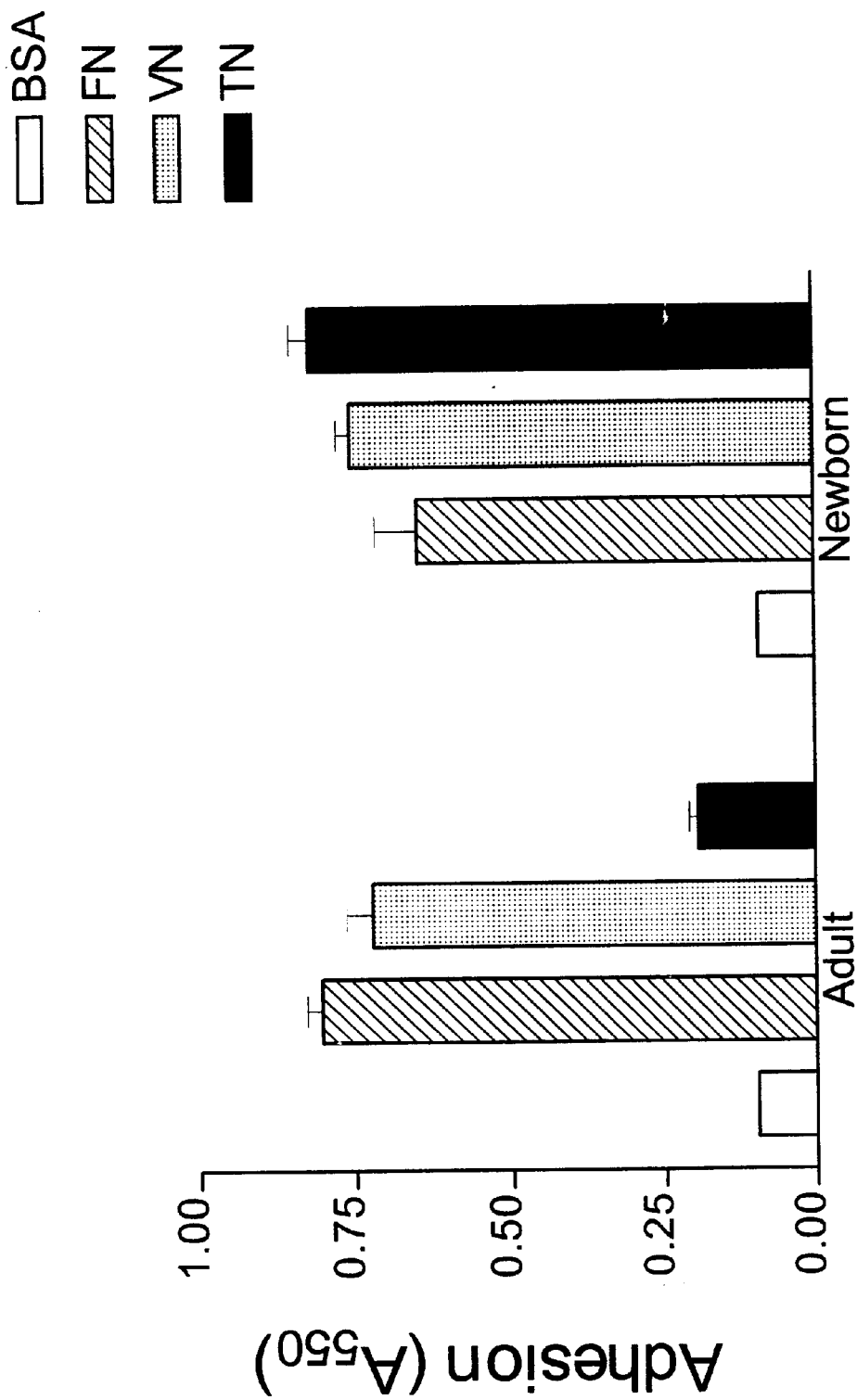
FIG. 1 shows adhesion of either adult or newborn aortic SMCs to the matrix proteins including intact fibronectin (FN), vitronectin (VN) or Tenascin-C (TN).

The present invention is based on the discovery that the Fbg-L domain of a Tenascin-C protein is involved in SMC adhesion and migration, and the active site of the Fbg-L domain may be mapped to a polypeptide. While not wanting to be bound by the theory, it has been observed that blocking the interaction of Fbg-L with SMC can inhibit SMC adhesion and migration. Therefore, it is believed that the active site(s) contained in the Fbg-L domain of Tenascin-C mediates SMCs adhesion and migration. Blocking this interaction may inhibit SMC migration from media into the neointima and ultimately affect neointimal formation.

Accordingly, the present invention provides a synthetic polypeptide derived from a Tenascin-C protein. The polypeptide is capable of interacting with smooth muscle cells. For the purpose of the present invention, a synthetic polypeptide is "derived from" Tenascin-C protein if it contains an amino acid sequence which corresponds to the amino acid sequence of a region of Tenascin-C protein. As used herein, the term "synthetic peptide" depicts a peptide which does not comprise an entire naturally occurring protein molecule. The peptide is "synthetic" in that it may be produced by human intervention using such techniques as chemical synthesis, recombinant genetic techniques, or fragmentation of whole protein or the like. The polypeptide is capable of interacting with smooth muscle cells if it can block or reduce the interaction of Tenascin-C with smooth muscle cells.

Minor modifications of the primary amino acid of the peptide of the present invention may result in a peptide which has substantially equivalent activity as compared with the specific peptide described herein. Such modifications may be deliberate, as by site-directed mutagenesis, or may be spontaneous. Modifications may also be made to the length of the peptide of the present invention. It is recognized by those skilled in the art that it is possible that a peptide which is longer or shorter than the peptide of the present invention may still preserve substantially the same biological function of the peptide of the present invention. All of the peptides produced by these modifications are included herein as long as the biological activity of the peptides are still present.

Peptides of the present invention can be synthesized by methods commonly known in the art. In one embodiment, polypeptides may be synthesized using Fmoc (N-(9-fluorenyl)methoxycarbonyl) strategies on an Advanced Chem Tech multiple synthesizer model 396, and purified by reverse phase high performance liquid chromatography. Other methods known in the art may also be used. For example, peptides can be prepared by solid-phase synthesis in a 430A Applied Biosystems (Foster City, Calif.) peptide synthesizer and purified to greater than 99% purity in a Waters HPLC (Waters Associates, Milford, Mass.). Other commonly used methods such as t-BOC or FMOC protection of alpha-amino groups may also be used. Both methods involve stepwise syntheses whereby a single amino acid is added at each step starting from the C terminus of the peptide (see, Coligan, et al., *Current Protocols in Immunology*, Wiley Interscience, 1991, Unit 9).

In one embodiment of the present invention, a synthetic polypeptide of the present invention is derived from the Fbg-L domain of the Tenascin-C protein, and containing an active site recognizable by SMC. Examples of such a synthetic polypeptide include, but are not limited to, polypeptides having, respectively, amino acid sequences of SEQ ID NO:3, SEQ ID NO:6. SEQ ID NO:8, and SEQ ID NO:9. The amino acid sequences of those polypeptides are set forth in FIG. 7. Preferably, a synthetic polypeptide of the present invention has an amino acid sequence of SEQ ID NO:8.

One aspect of the present invention provides an antibody against the peptides of the present invention. Antibodies provided in the present invention are immunoreactive or bind to the peptides of the present invention. Alternatively, they may bind to a region represented by the peptides of the present invention located on the Fbg-L domain of Tenascin-C. Antibodies of the present invention may also include any antibodies that bind to the Tenascin-C protein, whose binding reduces the interaction of Tenascin-C with SMC.

Antibodies which consist essentially of pooled monoclonal antibodies with different epitopic specificities, as well as distinct monoclonal antibody preparations are provided. Monoclonal antibodies are made from antigen containing peptides of the present invention by methods well known in the art (Kohler, et al., Nature, 256:495, 1975; Current Protocols in Molecular Biology, Ausubel et al., ed., 1989).

Antibodies which bind to the peptides of the present invention or a region of Tenascin-C can be prepared using an intact polypeptide or fragments containing peptides of interest as the immunizing antigen. A polypeptide used to immunize an animal can be derived from translated cDNA or chemical synthesis, purified and conjugated to a carrier protein, if desired. Such commonly used carriers which are chemically coupled to the peptide include keyhole limpet hemocyanin (KLH), thyroglobulin, bovine serum albumin (BSA), and tetanus toxoid. The coupled peptide is then used to immunize the animal (e.g., a mouse, rat, or rabbit).

If desired, polyclonal antibodies can be further purified, for example, by binding to and eluding from a matrix to which a polypeptide or a peptide to which the antibodies were raised is bound. Those of skill in the art are familiar with the various techniques common in the immunology arts for purification and/or concentration of polyclonal antibodies, as well as monoclonal antibodies (e.g., Coligan, et al., Unit 9, Current Protocols in immunology, Wiley Interscience, 1991, incorporated by reference).

The term "antibody" as used in this invention includes intact molecules as well as fragments thereof, such as Fab, F(ab')$_2$, and Fv, which are capable of binding to the epitopic determinant. These antibody fragments retain some ability to selectively bind with their antigen or receptor, and are defined as follows:

(1) Fab, the fragment which contains a monovalent antigen-binding fragment of an antibody molecule can be produced by digestion of whole antibody with the enzyme papain to yield an intact light chain and a portion of one heavy chain;
(2) Fab', the fragment of an antibody molecule can be obtained by treating a whole antibody with pepsin, followed by reduction, to yield an intact light chain and a portion of the heavy chain; two Fab' fragments are obtained per antibody molecule;
(3) (Fab')2, the fragment of the antibody that can be obtained by treating a whole antibody with the enzyme pepsin without subsequent reduction; F(ab')2 is a dimmer of two Fab' fragments held together by two disulfide bonds;
(4) Fv, defined as ia genetically engineered fragment containing the variable region of the light chain and the variable region of the heavy chain expressed as two chains; and,
(5) Single chain antibody ("SCA"), defined as a genetically engineered molecule containing the variable region of the light chain and the variable region of the heavy chain, linked by a suitable polypeptide linker as a genetically fused single chain molecule.

Methods of making these fragments are known in the art. (e.g., Harlow and Lane, Antibodies: A Laboratory Manual, Cold Spring Harbor Laboratory, New York (1988), incorporated herein by reference.)

Another aspect of the present invention provides a method of inhibiting the Tenascin-C protein mediated SMCs adhesion and migration. The method includes contacting the SMCs with an effective amount of a factor capable of reducing the interaction of the SMC, with the Tenascin-C protein. The amount of the factor is effective if the factor can inhibit the Tenascin-C protein mediated SMCs adhesion and migration. The determination of the effective amount of the factor is well within the skill in the art in view of the instant disclosure.

The factor can be any factor that is capable of reducing the interaction of the SMC with the Tenascin-C protein. In one embodiment of the present invention, the factor is a synthetic polypeptide of the present invention, derived from the Tenascin-C protein. Examples of the polypeptide include, but are not limited to, a polypeptide which contains a Fbg-L domain of the Tenascin-C protein, polypeptides having, respectively, amino acid sequences of SEQ ID NO:3, SEQ ID NO:6, SEQ ID NO:8, and SEQ ID NO:9. Preferably, the polypeptide has an amino acid sequence of SEQ ID NO:8.

In another embodiment of the present invention, the factor is an antibody of the present invention. The antibody can be any antibody of the present invention that recognizes the Tenascin-C protein, and that can bind to the Tenascin-C protein to reduce the interaction of the Tenascin-C protein with SMCs. The antibody can be a polyclonal antibody or a monoclonal antibody.

In accordance with another embodiment of the present invention, the factor can be a chemical compound that is capable of reducing the interaction of the Tenascin-C protein with SMCs. Example, of the chemical compound include, but are not limited to, ethylene diaminetetra acetic acid (EDTA) and any other chelating agent that can trap cations such as $Mg_{2+}$.

A further aspect of the present invention provides a method of inhibiting Tenascin-C mediated smooth muscle cell adhesion and migration in a host comprising the step of administering to the host in need of the inhibition an effective amount of a factor capable of reducing the interaction of the SMC with the Tenascin-C protein. Preferably, the administration is for the treatment of intimal hyperplasia, restenosis, and atherosclerosis. The term "inhibit" as used herein includes its generally accepted meaning which includes phrophylactically treating a host such as a human subject to incur smooth muscle cell migration, and holding in check and/or treating existing smooth muscle cell migration.

In one embodiment of the present invention, the factor is a synthetic polypeptide of the present invention, derived from Tenascin-C protein. Examples of the polypeptide include, but are not limited to, a polypeptide which contains a Fbg-L domain of the Tenascin-C protein, and polypeptides having, respectively, amino acid sequences of SEQ ID NO:3, SEQ ID NO:6, SEQ ID NO:8, and SEQ ID NO:9. Preferably, the polypeptide has an amino acid sequence of SEQ ID NO:8.

In another embodiment of the present invention, the factor is an antibody of the present invention. The antibody can be any antibody of the present invention that recognizes the Tenascin-C protein and binds to the Tenascin-C protein to reduce the interaction of the Tenascin-C protein with SMCs. The antibody can be a polyclonal antibody or a monoclonal antibody.

The antibodies of the invention can be administered parenterally by injection or by gradual infusion over time. The monoclonal antibodies of the invention can be administered intravenously, intraperitoneally, intramuscularly, subcutaneously, intracavity, or transdermally. In one embodiment of the present invention, the antibodies are administered through continuous intravenous infusion.

The peptides of the present invention can be administered by methods described for administration of the monoclonal antibodies. Preferred methods for delivery of the peptide include oral administration, by encapsulation in microspheres or proteinoids, by aerosol delivery to the lungs, or transdermally by iontophoresis or transdermal electroporation. Other methods of administration will be known to those skilled in the art. For instance, in one embodiment of the present invention, peptides of the present invention are delivered through a perivascular delivery system as described by Choi, E. T. et al., *J. Vasc. Surg.*, 19(1): 125–134 (1994), the content of which is incorporated herein by reference.

The amount of the factor is effective if the factor can inhibit Tenascin-C mediated SMCs adhesion and migration in the host. It is to be understood that the effective amount may vary depending on, inter alia, the unique characteristics of the factor, the individual host, the chosen administration regimen as is well known in the art. In one embodiment, peptides may be administered continuously through a perivascular delivery system at about 1 to 3 μg/hr for a period of time that is necessary to achieve a concentration of above 20 μg/ml. Antibodies may be administered to a host through continuous intravenous infusion at a rate of about 30 to 40 μg/day for about 5–8 days. The determination of the effective amount of the factor is well within the skill in the art in view of the instant disclosure.

The present invention also provides a pharmaceutical composition comprising a therapeutically effective amount of a factor capable of reducing the interaction of the SMC with the Tenascin-C protein, and a pharmaceutically acceptable carrier. The factor can constitute either the peptides or the antibodies of the present invention. Preferably, the factor is a synthetic polypeptide having an amino acid sequence of SEQ ID NO:8.

Preparations for parenteral administration of a peptide or an antibody of the invention include sterile aqueous or non-aqueous solutions, suspensions, and emulsions. Examples of non-aqueous solvents are propylene glycol, polyethylene glycol, vegetable oils such as olive oil, ;and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers and electrolyte replenishers, such as those based on Ringer's dextrose. Preservatives and other additives may also be present such as antimicrobials, antioxidants, chelating agents, inert gases, and the like.

The following examples are intended to illustrate but not limit the invention. While they are typical of those that might be used, other procedures known to those skilled in the art may alternatively be used.

EXAMPLE I

EXPERIMENTAL PROCEDURES AND METHODOLOGY

A. Materials

Tenascin-C was purified from conditioned media of BHK cells overexpressing Tenascin-C, as described (10). The recombinant proteins corresponding to the full-length Fbg-L and FN-L domains were expressed and purified from the bacteria BL-21 $E.\ coli$ provided by Dr. Harold Erickson (Duke University). Dr. John Peters (Cedars-Sinai Med. Ctr.) kindly provided the recombinant fibronectin type III unit 10. Pre-stained protein standards were obtained from Bio-Rad, Richmond, Calif. Other chemicals were of reagent grade quality and were obtained from Sigma.

B. Cell culture

Adult Aortic SMCs were cultured as described (12). Newborn (9-day old) aortic SMCs were obtained from Dr. Stephen, M. Schwartz, of University of Washington, and subsequently cultured (13). Briefly, rat aortic SMCs were isolated by enzymatic digestion of rat aorta (Sprague-Dawley, 2 months old, 270 g). Cells were grown in DMEM/F12 media (Gibco) supplemented with 10% fetal bovine serum (Gibco). After reaching confluence, cells (between $3^{rd}$ and $6^{th}$ passages) were used for adhesion studies.

C. Adhesion assay

Microtiter plates (Falcon, Becton Dickinson, Oxnard, Calif.) were coated with the respective substrate for one (1) hour at 37° C. Nonspecific sites were blocked with 1 mg/ml BSA in PBS. Subconfluent cells exhibited higher adhesion activity than confluent cultured cells; therefore, cells were split and plated at half confluence the day before the assay. SMC subtypes were detached by trypsin/EDTA, washed once in DMEM/F12 media, 2.5 mg/ml BSA and 1 mg/ml trypsin inhibitor (adhesion buffer) and plated at $4 \times 10_4$ cells per well. After incubation for 60 min. at 37° C., nonadherent cells were removed with gentle washing with PBS. The number of attached cells were quantified by staining cells with 0.2% crystal violet in 20% methanol, lysing with 1% SDS, and measuring the absorbance at 550 nm (14).

To determine the concentration for the adhesion assays, microtiter plates were coated with increasing concentrations (1–100 µg/ml) of substrates, and the number of adherent cells was quantified. Adhesion of cells to Tenascin-C reached saturation levels at coating concentrations of 10 µg/ml (not shown). Therefore, all the subsequent adhesion assays were performed by coating the wells with a 10 µg/ml substrate.

D. Expression of recombinant FN-L subdomains

The PET expression system was used to express the recombinant FN-L subdomains (21). The primers were targeted to the exact boundaries of the alternatively spliced fibronectin type III repeats corresponding to each isoform of Tenascin-C. A BamHI site together with the NdeI site provided for unidirectional ligation downstream from the T7 promoter in the expression vector pET11 a (Novagen, Madison, Wis.). The cloned subunits were resequenced to ensure that no errors had been introduced during the cloning process. The resultant construct was transformed into the $E.\ coli$ expression host BL21 (DE3) (Novagien). Clonal cultures were grown in LB media, containing 50 µg/ml carbenicillin, and induced with IPTG for 3 hours. Polyclonal antibodies to Tenascin-C were used to identify the recombinant proteins. To further assess the integrity of the recombinant proteins, their amino acid composition and partial amino acid sequence were determined (UCLA Amino Acid Sequencing Core Facility). Both corresponded exactly to the predicted values (not shown).

E. Peptide Synthesis

Peptides corresponding to the full-length Fbg-L domain were synthesized in the UCLA Peptide Synthesis Core Facility. The peptides were synthesized using FMOC strategies on an Advanced Chem. Tech. Multiple Synthesizer Model 396, cleaved at room temperature (cleavage mixture: 90% trifluoroacetate, 5% thioanisol, 3% ethanedithiol, 2% anisole), purified by reverse phase HPLC, and characterized by mass spectral analysis (at the UCLA Mass Spectroscopy Facility) and high performance capillary electrophoresis (Beckman 2200 HPCE). The Core Facility was unable to synthesize peptides II and VII, presumably due to the formation of a strong secondary structure, which prevented elongation of the peptide chain.

F. Migration assay

Cell migration was measured by a modification of the Boyden's chamber method using microchemotaxis chambers (Neuro Probe Inc.). Polycarbonate filters were coated with 10 µg/ml of substrates overnight at 4° C. Newborn rat SMCs were suspended at a concentration of $10_5$ cells/ml in serum-free DMEM supplemented with 1 mg/ml BSA. A volume of 50 µl of cell suspension was placed in the upper chamber, and 30 µl of 10% bovine calf serum in DMEM was placed in the lower chamber. In some experiments, cells were suspended in DMEM supplemented with 0.1 µM of the fibrinogen-like domain (Fbg-L) or 1 µM of peptide VIII before addition to the upper chamber. The chamber was incubated at 37° C. under 5% $CO_2$ in air for 4 hours. The filter was removed, and the cells on the upper side of the filter were scraped off. The SMCs that had migrated to the lower side of the filter were fixed in methanol, stained with Diff-Quick staining solution (Baxter) and counted under a microscope.

EXAMPLE II

EFFECT OF TENASCIN-C ON CELL ADHESION IN DIFFERENT SMC SUBTYPES

Interaction between aortic SMCs and Tenascin-C was assessed by an adhesion assay. FIG. 1 shows the adhesion of SMCs to the matrix proteins. In FIG. 1, 96-well plates were coated with solutions containing intact fibronectin (FN), vitronectin (VN) or Tenascin-C (TN) and incubated with either adult or newborn aortic SMCs. Adhesion is measured by determining absorbance of attached cells after staining with crystal violet. Values shown are from a representative experiment in which triplicates are plotted as mean±SEM.

FIG. 1 shows that adult rat aortic SMCs avidly adhered to wells coated with fibronectin and vitronectin. By contrast, adhesion to Tenascin-C was 3–4 times lower than attachment to the adhesive proteins. Tenascin-C-adherent cells remained round, whereas spreading and flattening followed attachment to fibronectin and vitronectin (not shown). The reduced adhesion of adult SMCs with Tenascin-C indicates that either complete binding equilibrium did not occur at 60 min. or that adult SMCs have a diminished ability to interact with Tenascin-C. We found that the interaction reached equilibrium levels at 60 min (not shown). Therefore, the reduced SMC-Tenascin-C interaction most likely reflects lower adhesive capacity of adult SMCs for Tenascin-C.

Without being bound by the theory, since Tenascin-C is prominently expressed during embryogenesis (19, 22), it was postulated that SMCs derived from newborn arteries might express a higher number of Tenascin-C receptors. In order to explore this possibility, the adhesion of cultured newborn SMCs to Tenascin-C was examined (FIG. 1). FIG. 1 shows that the levels of adhesion of newborn SMCs to Tenascin-C were 3–4 times higher than adult cells and were comparable to the attachment levels observed with fibronectin (FIG. 1).

EXAMPLE III

THE ROLE OF RGD MOTIF IN CELL BINDING

Figure 2:
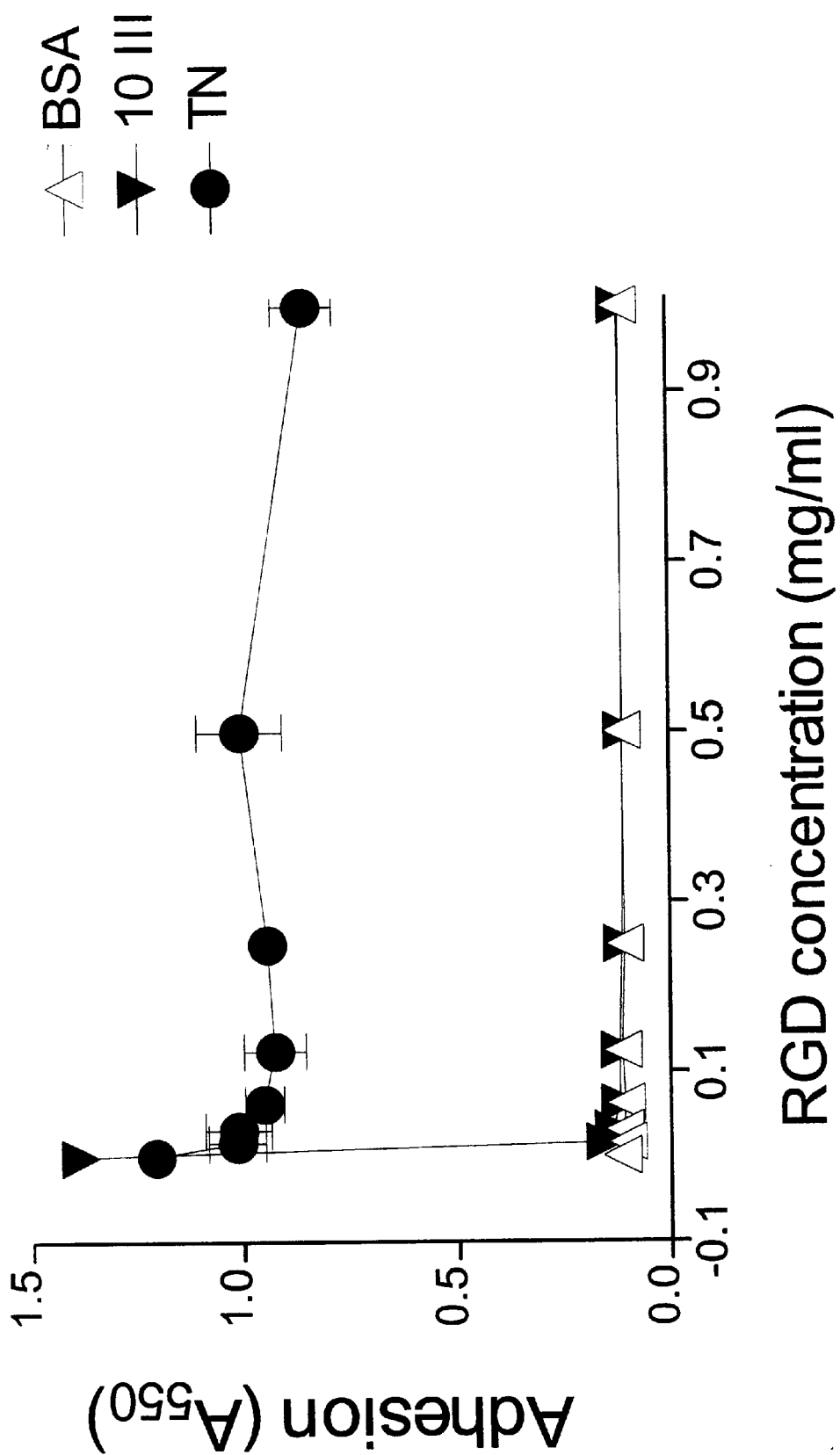
FIG. 2 shows the effect of RGD peptide on the interaction between newborn SMCs and Tenascin-C.

It has been shown that the interaction of some cells with Tenascin-C is mediated by the RGD motif (20, 23). Therefore, an adhesion assay was used to determine the role of RGD in the interaction between Tenascin-C and SMCs. The specificity of the adhesion was determined by coating the wells with the recombinant 10th-type III repeat of fibronectin (24). In FIG. 2, 96-well plates were coated with either BSA (BSA), Tenascin-C (TN), or the recombinant 10th-type III repeat of fibronectin (10III) as described for FIG. 1. Newborn SMCs were detached, washed once in adhesion buffer and added to various concentrations of the peptide GRGDS (SEQ ID No: 10. Cells and peptides were then preincubated for 30 min. prior to plating. The values shown are the mean±SEM of triplicate samples. Nonspecific binding to control wells coated with BSA was not subtracted from each value.

As shown in FIG. 2, a GRGDS, SEQ ID NO: 10 peptide inhibited the attachment of newborn SMCs to the recombinant fibronectin fragment, and complete inhibition was observed at 0.1 mg/ml. Attachment of SMCs to Tenascin-C was inhibited by approximately 30% in the presence of 0.1 mg/ml GRGDS, SEQ ID NO: 10 peptide, and higher concentrations did not significantly alter adhesion levels (FIG. 2). To establish the sequence specificity of the RGD-mediated interaction, the effect of the GRGDS, SEQ ID NO: 10 peptide was compared with an inactive GRFDS (SEQ ID NO: 11) peptide. The GRFDS, SEQ ID NO: 11 peptide had no effect (not shown), demonstrating that the RGD-mediated interaction of Tenascin-C is specific.

EXAMPLE IV

EFFECT OF CATIONS ON THE INTERACTION BETWEEN SMCS AND TENASCIN-C

Figure 3:
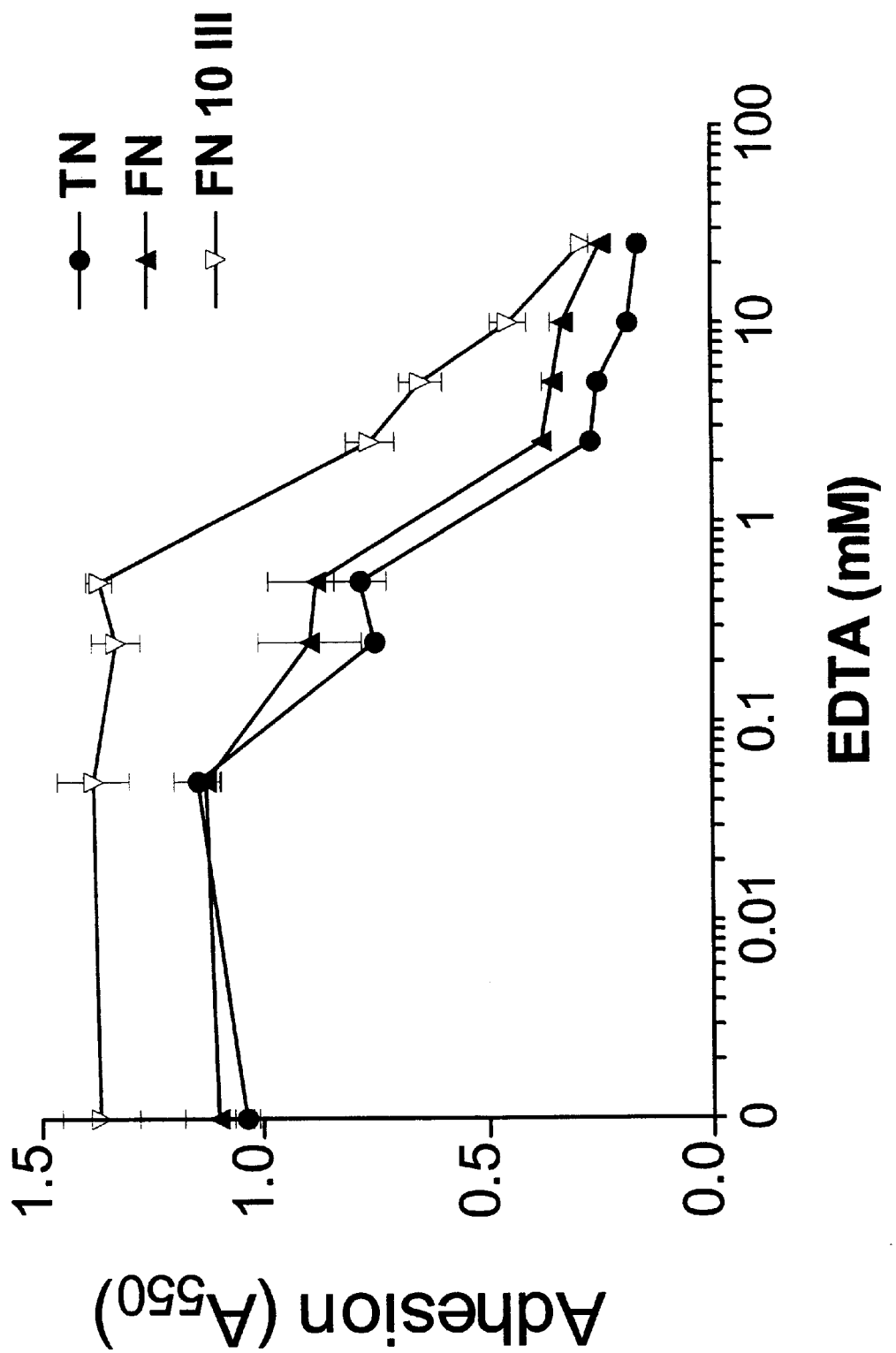
FIG. 3 shows the effect of EDTA on the adhesion of newborn SMCs to Tenascin-C.

To determine the role of cations in the interaction between SMCs and Tenascin-C, the adhesion assay was performed in the presence of increasing concentrations of EDTA (FIG. 3). In FIG. 3, 96-well plates were coated with solutions containing intact fibronectin (FN), the recombinant 10th-type III repeat of fibronectin (FN10III), or Tenascin-C (TN). Newborn SMCs were detached, washed once with adhesion buffer, added to various concentrations of EDTA, and plated. The number of attached cells was quantified by a colorimeter. Values shown are from a representative experiment in which triplicates are plotted as mean±SEM.

The intact fibronectin molecule and its recombinant subunit were used as a positive control. Newborn Sells adhered well to Tenascin-C, fibronectin, or the recombinant fragment in the absence of EDTA. Addition of 1 mM EDTA reduced the adhesion of newborn cells to the intact fibronectin molecule or Tenascin-C by 50%, and nearly complete inhibition of cell adhesion to all substrates was observed with 10 mM EDTA. These results suggest that cations are essential for adhesion of newborn SMCs to Tenascin-C.

Figure 4:
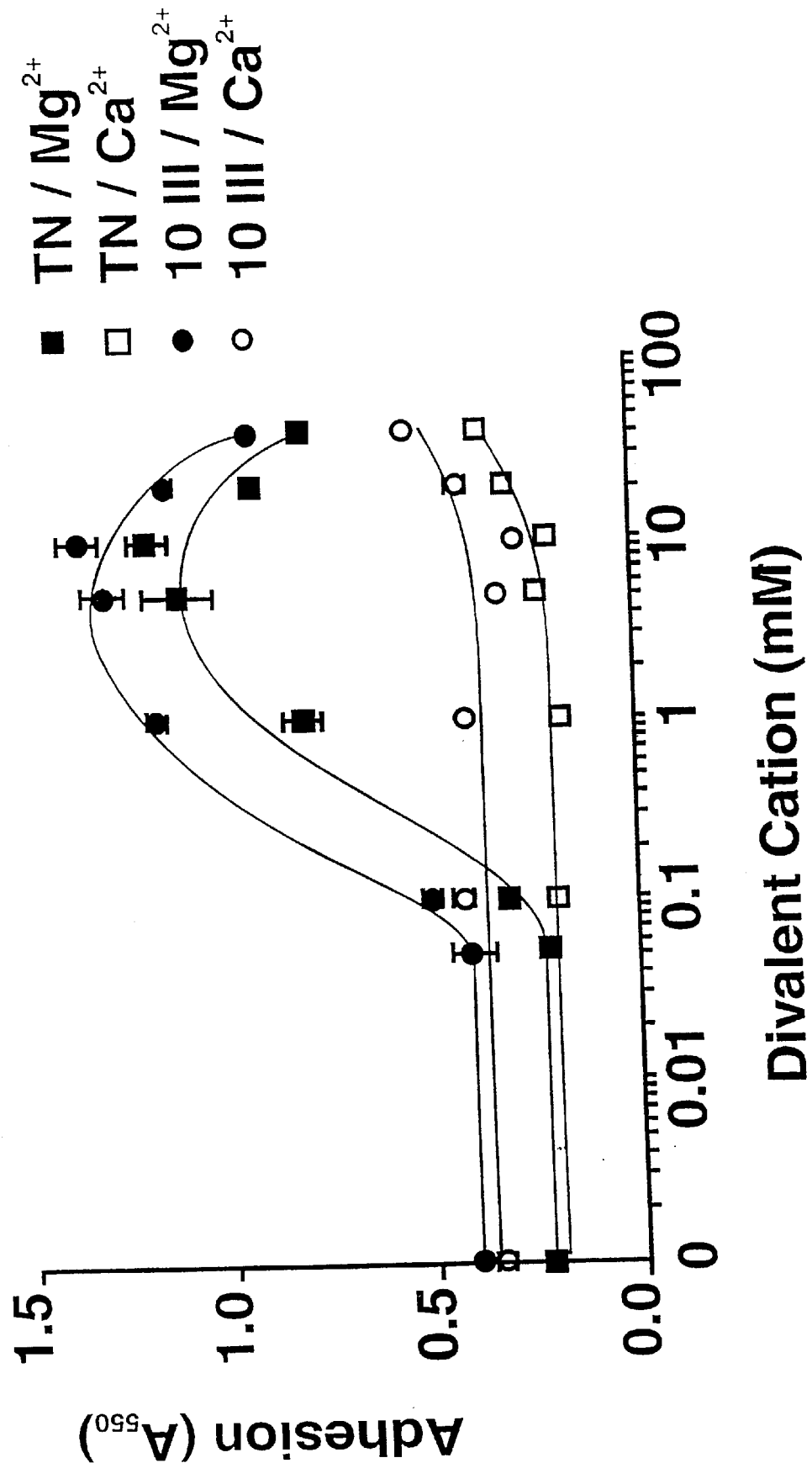
FIG. 4 shows the effect of $Mg^{2+}$ and $Ca^{2+}$ on the interaction of newborn SMCs with Tenascin-C.

Consequently the type of cation markedly affects the association rate constant of ligand for integrin (25–27). To determine which cation influences the adhesion of SMCs to Tenascin-C, the effect of both $Ca^{2+}$ and $Mg^{2+}$ cations on cell adhesion was examined. In FIG. 4, 96-well plates were coated with either Tenascin-C (TN) or the recombinant tenth type III repeat of fibronectin (10III) as described for FIG. 1. Newborn SMCs were detached, washed once in the adhesion buffer, added to various concentrations of either $Ca^{2+}$ or $Mg^{2+}$, and plated. Values shown are from the mean±SD of triplicate samples. Nonspecific binding to BSA-coated control wells was not subtracted and was 0.23±SEM.

FIG. 4 shows that the level of newborn SMCs adhesion to Tenascin-C or the recombinant fibronectin fragment increased as the $Mg^{2+}$ concentration increased. Maximal cell adhesion to both substrates was observed in the range of 5–10 mM $Mg^{2+}$. In contrast, $Ca^{2+}$ was ineffective. Thus, it was concluded that there is a three-fold increase potential for the interaction between newborn SMCs and Tenascin-C in the presence of $Mg^{2+}$.

Since $Ca^{2+}$ ion can reverse the $Mg^{2+}$-dependent adhesion of some integrins, particularly $\alpha_2\beta_1$ (25), its effect on the adhesion of newborn SMCs to Tenascin-C in the presence of $Mg^{2+}$ cation was examined. There was no indication that the presence of $Ca^{2+}$ up to 10 mM, a concentration that completely reversed the $Mg^{2+}$-dependent adhesion of human fibroblast (28), could inhibit the $Mg^{2+}$-dependent adhesion of newborn cells (not shown).

EXAMPLE V

MAPPING OF THE ACTIVE DOMAIN OF TENASCIN-C

Figure 5:
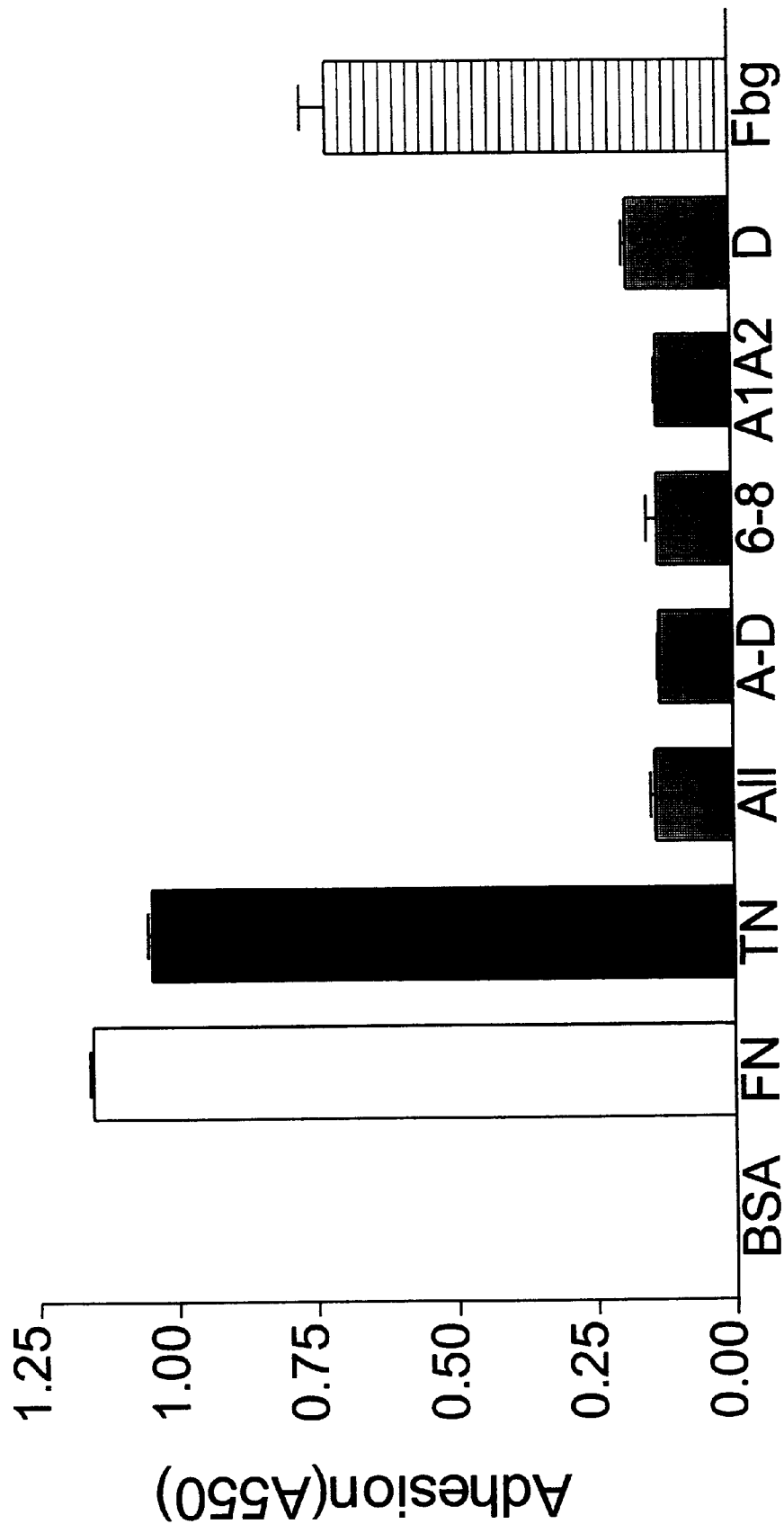
FIG. 5 shows the results of mapping the active domain of Tenascin-C.

The active domain of Tenascin-C was mapped using recombinant proteins corresponding to full-length Fbg-L and FN-L domains as well as FN-L subdomains 6–8, A-D, A1A2, and D. The ability of these domains, or subdomains, to interact with newborn SMCs was determined by an adhesion assay, and the results are shown in FIG. 5. In FIG. 5, a microtiter plate was coated with BSA, fibronectin (FN), intact Tenascin-C (TN), and the recombinant proteins corresponding to: the Fbg-L domain (Fbg-L), the entire FN-L repeats (All), the constitutively spliced repeats 6–8, the alternatively spliced A-D, A1A2, and D domains. An adhesion assay was performed with newborn SMCs. Values shown are from a representative experiment in which triplicates are plotted ±SEM.

FIG. 5 shows that the level of adhesion to the intact Tenascin-C molecule was high compared to the fibronectin.

Newborn cells adhered to the Fbg-L domain, and although the level of adhesion was slightly lower, it was comparable to the intact Tenascin-C. In contrast, SMCs did not adhere either to the entire FN-L domain or its recombinant subdomains. As with the intact Tenascin-C, the Fbg-L-adherent cells remained round and did not spread (not shown). Similar results were obtained with adult SMCs, although the level of adhesion to the Fbg-L domain was markedly lower (not shown).

Figure 6:
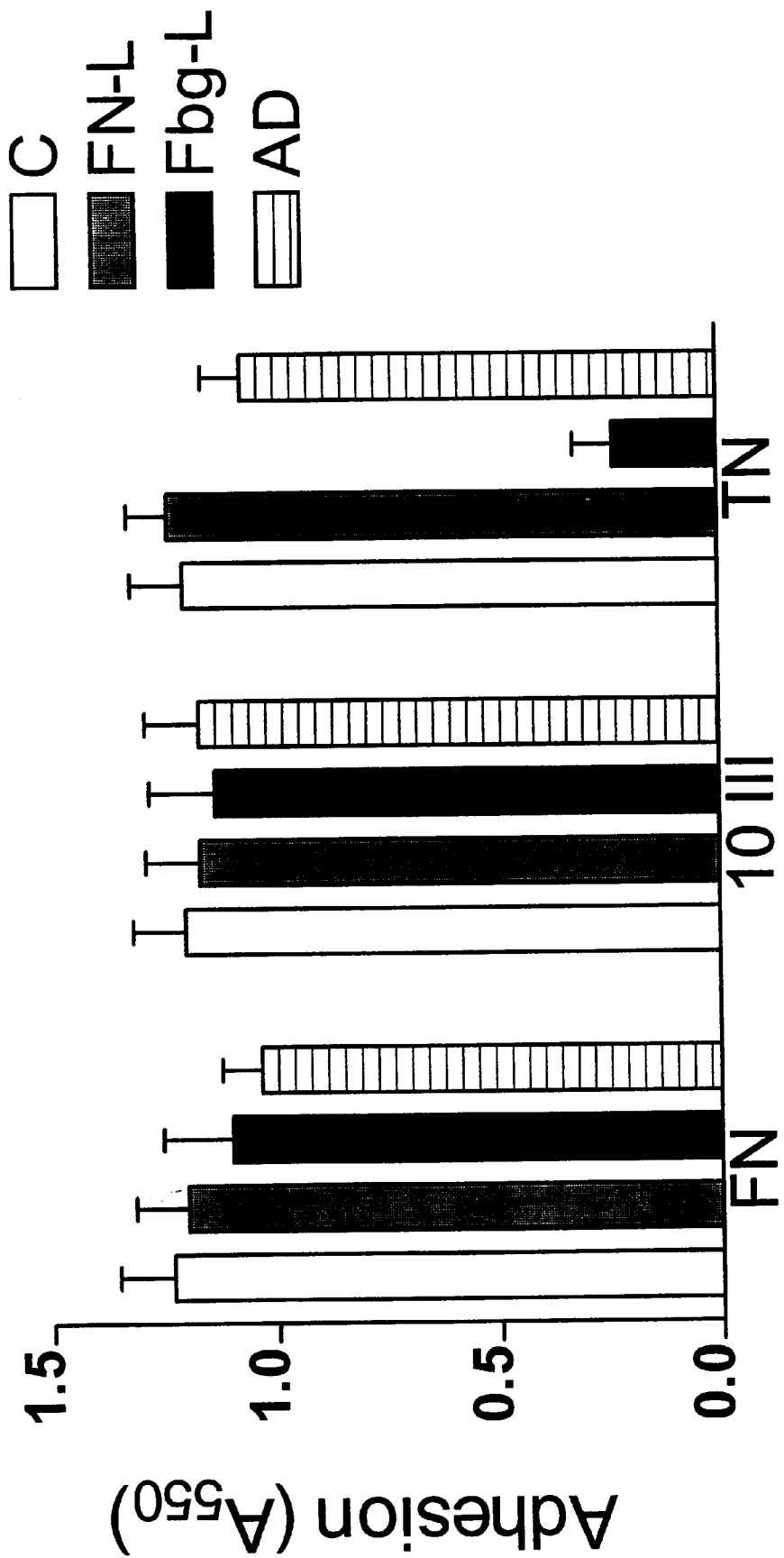
FIG. 6 shows the effect of the soluble Tenascin-C domains on newborn SMC adhesion.

The inability of FN-L domain or subdomains to promote cell adhesion could be explained by the reduced capacity of the FN-L repeats to coat tissue culture dishes, by the loss of function as a result of binding to tissue culture dishes, or by the lack of activity of the FN-L domains. To distinguish between these possibilities, the recombinant FN-L proteins were labeled with $^{125}$I, and their ability to coat the tissue culture dishes was compared to the Fbg-L domain. There was no difference in the coating efficiency of these recombinant proteins (not shown). To determine whether the binding to tissue culture dishes had influenced the activity of the recombinant proteins, the ability of soluble Fbg-L or FN-L domains and subdomains to inhibit the interaction between intact Tenascin-C and SMCs was examined. FIG. 6 summarizes the results. In FIG. 6, 96-well plates were coated with fibronectin (FN), the recombinant tenth type III repeat of fibronectin (10III), or an intact Tenascin-C molecule (TN). Newborn SMCs were incubated for 15 min. at 37° C. with a solution of 200 μg/ml of a recombinant Fbg-L domain, the entire FN-L domain (FN-L), or the alternatively spliced A-D repeats (AD). Control cells had only BSA (C). Adhesion was measured as described above. Values shown are from representative experiments in which triplicates are plotted ±SEM. FIG. 6 indicates that the soluble FN-L domain or subdomains were inactive, whereas 200 μg/ml soluble Fbg-L reduced adhesion of SMCs to Tenascin-C by 70%. The soluble recombinant Fbg-L had no effect on the adhesion of SMCs to either intact fibronectin or its recombinant fragment. Further, adhesion of SMCs to the Fbg-L domain was controlled by the same factors that regulated adhesion of cells to Tenascin-C, i.e., adhesion was completely inhibited by EDTA and promoted by a $Mg^{2+}$ cation, but not $Ca^{2+}$ (not shown). Taken together, this data led to a conclusion that the Fbg-L domain, but rot the FN-L domain, mediates adhesion of SMCs to Tenascin-C.

EXAMPLE VI

MAPPING OF THE ACTIVE SITE OF Fbg-L DOMAIN

To map the active site of the Fbg-L domain, nine synthetic peptides were designed. Each of the nine synthetic peptides contained a sequence of thirty (30) amino acids, and the nine (9) peptides together constituted the entire isolated Fbg-L domain. Some degree of overlap was included to avoid the possibility of splitting the active site and thereby losing the activity (FIG. 7). FIG. 7 shows the amino acid sequences of peptides I through IX, and the overlapping sequences have been underlined.

Figure 8:
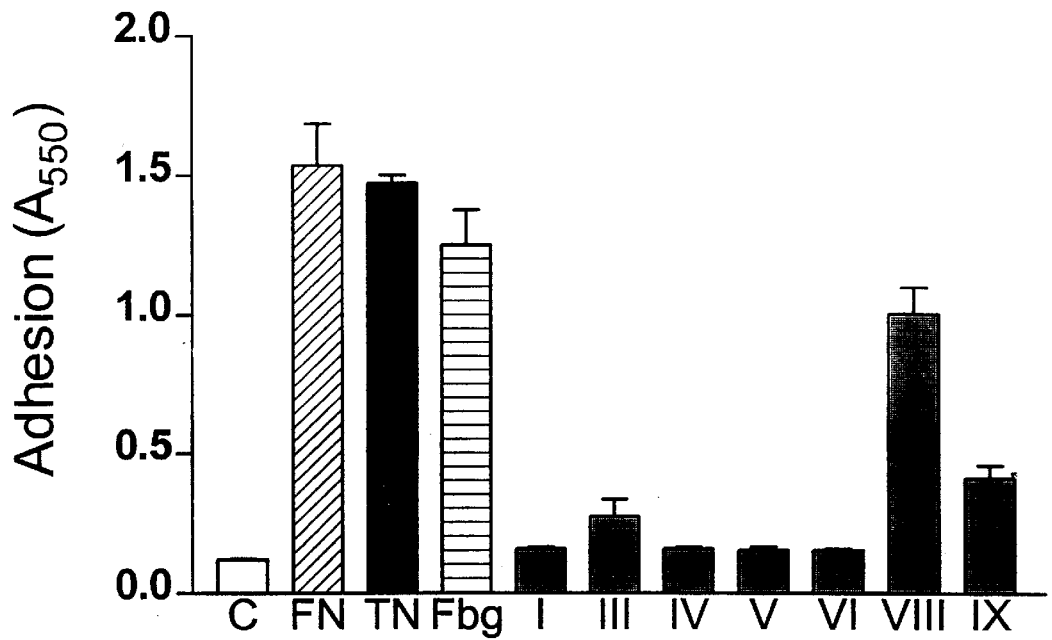
FIG. 8(A) shows the effect of synthesized peptides on the interaction between newborn SMCs and Tenascin-C.
FIG. 8(B) shows the effect of soluble peptides on the interaction between SMCs and intact Tenascin-C or the recombinant fibrinogen-like domain.
Figure 8:
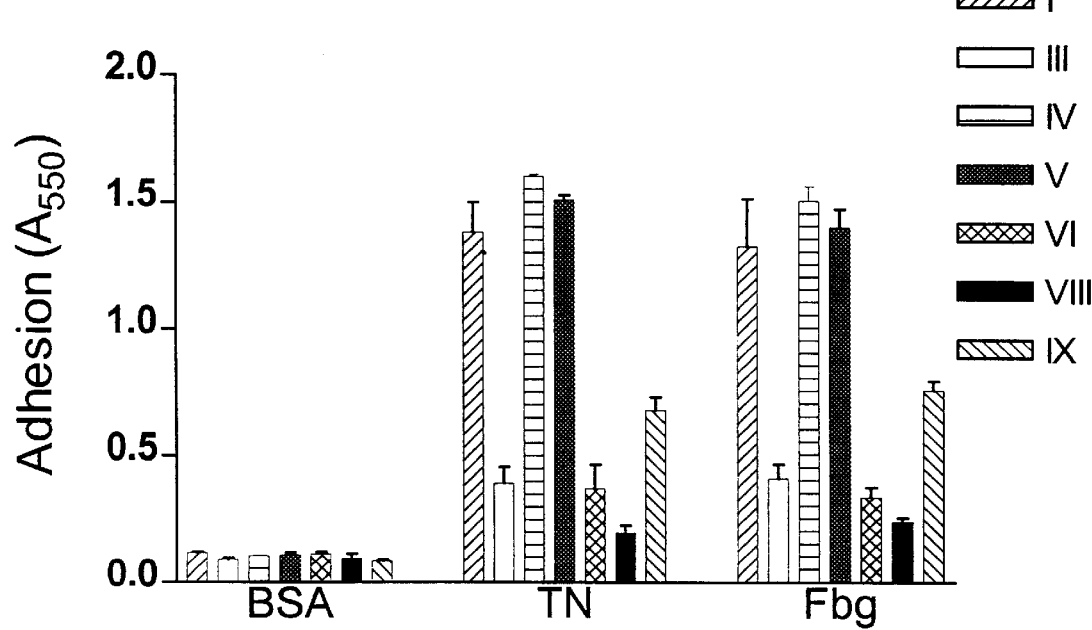

The ability of the synthetic peptides to directly interact with newborn cells was determined by an adhesion assay. FIG. 8(A) shows the effect of synthesized peptides on the interaction between newborn SMCs and Tenascin-C. In FIG. 8, 96-well plates were coated with solutions containing BSA (C), fibronectin (FN), Tenascin-C (TN), the fibrinogen-like domain (Fbg-L), and synthetic peptides at a concentration of 10 μg/ml in PBS. An adhesion assay was performed with newborn rat SMCs. Tissue culture plates were coated with increasing concentrations of peptides from 0.1 to 10 μg/ml, and the adhesion of newborn cells was measured. Values shown are from a representative experiment in which triplicates are plotted as mean±SEM.

Tissue culture plates were coated with increasing concentrations of peptides from 0.1 to 10 μg/ml, arid the adhesion of newborn cells measured. Cell adhesion was promoted as peptide concentration was increased from 0.1 to 1 μg/ml (not shown). Adhesion reached saturation levels at 1 μg/ml, and no significant change was observed beyond 10 μg/ml. Therefore, tissue culture plates were coated with a solution of 10 μg/ml of peptides in all subsequent experiments.

As shown ir FIG. 8(A), peptide VIII was the only peptide capable of strongly promoting newborn cell adhesion when coated on the tissue culture dishes, and it accounted for most (80%) of the adhesion activity of the Fbg-L domain. Peptide IX exhibited 30% activity, and other peptides were inactive. Similar to the interaction with intact Tenascin-C or the isolated Fbg-L domain, peptide VIII-adherent cells remained round. Further, as with the whole Fbg-L domain, adhesion to peptide VIII was blocked by EDTA and promoted by $Mg^{2+}$ (not shown).

The inability cf other peptides to promote SMCs adhesion suggests that peptide VIII was the only peptide that matched the active site of the Fbg-L domain. However, the possibility that either other peptides did not bind to tissue culture dishes, or that they lost their function as a result of binding to tissue culture dishes, cannot be entirely eliminated. It was found that there was no difference in the ability of peptides to coat tissue culture dishes (not shown). To determine whether peptides lose their function as a result of binding to tissue culture dishes, an adhesion assay was performed in the presence of soluble peptides. FIG. 8(B) shows the effect of soluble peptides on the interaction between SMCs and intact Tenascin-C or the recombinant fibrinogen-like domain. In FIG. 8(B), 96-well plates were coated with BSA, intact Tenascin-C (TN) or the fibrinogen-like domain (Fbg-L), and adhesion of newborn cells was measured in the presence of 1 μM synthetic peptides.

As shown in FIG. 8(B), in addition to peptide VIII, soluble peptides III and VI completely blocked adhesion of newborn cells to either intact Tenascin-C or the Fbg-L domain. Other peptizes were either partially active (IX) or were completely inactive (I, IV, V). This suggests that peptide III or VI may lose their function as a result of conformational changes induced after binding to tissue culture dishes. If true, these peptides may represent a sensitive active site. It is thus unclear whether these sites remain active when soluble Tenascin-C is incorporated into the insoluble extracellular matrix substrate.

To assess the specificity of adhesion to peptide VIII, the ability of the soluble Fbg-L domain to inhibit SMCs adhesion to peptide VIII was evaluated. An adhesion assay was performed in the presence of increasing concentrations of the soluble Fbg-L domain from 50–500 μg/ml. It was found that 250 μg/ml of the soluble Fbg-L domain reduced adhesion of SMCs to the Fbg-L domain and peptide VIII by 70% and 80%, respectively. In contrast, the entire FN-L domain or the A1A2 subdomain had no effect (not shown).

Figure 9:
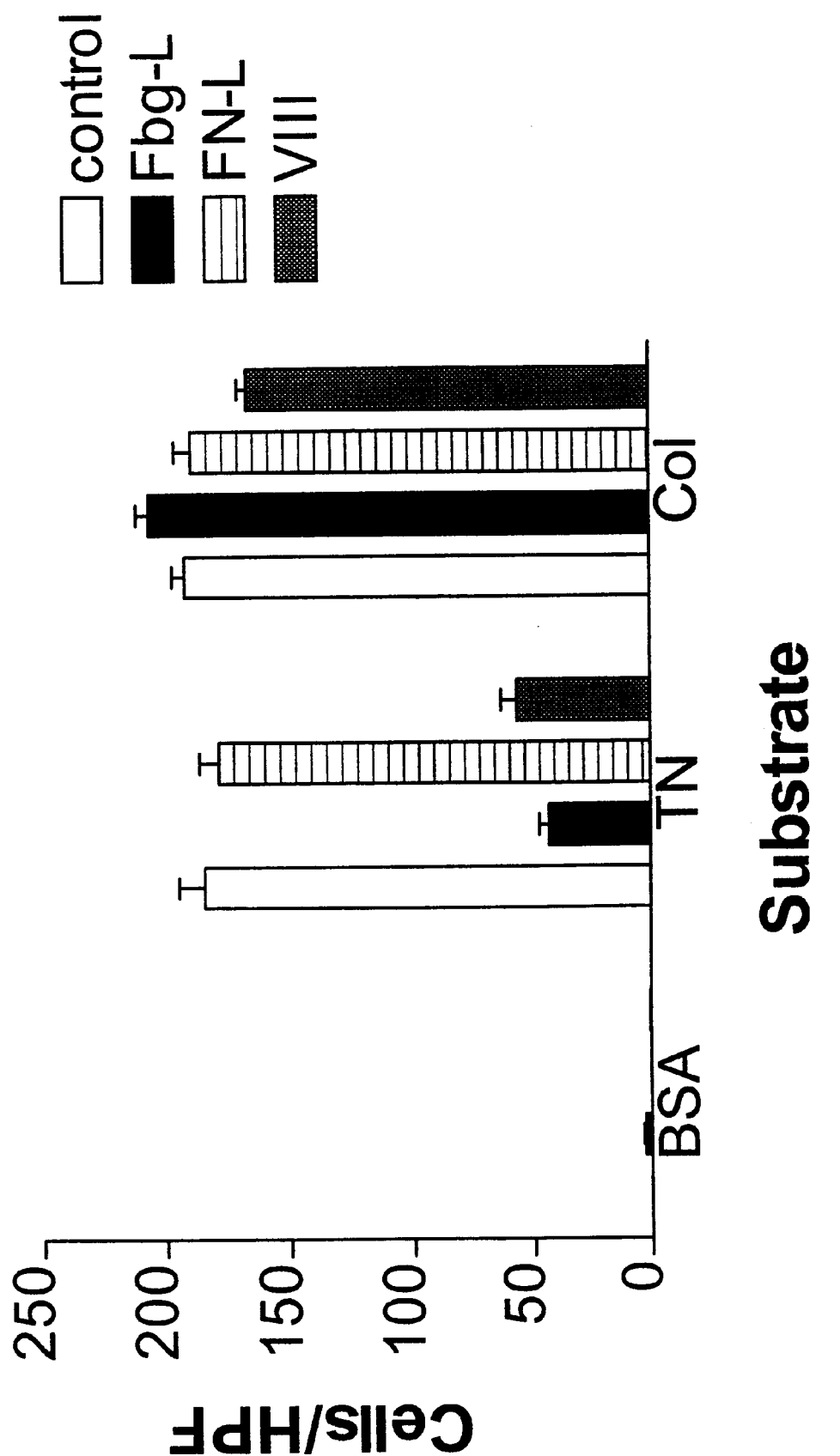
FIG. 9 shoves the effect of peptide VIII on newborn cell migration.

To map the active domain of Tenascin-C that is involved in cell migration, the ability of the recombinant domains to block SMCs migration on a Tenascin-C substrate was determined. FIG. 9 shows the effect of peptide VIII on newborn cell migration. In FIG. 9, cell migration was measured by a modification of Boyden's chamber. Polycarbonate filters were coated with BSA, Tenascin-C (TN), or collagen (Col)

substrates. Newborn rat SMCs were placed in the upper chamber and BSA was placed in the lower chamber. In some experiments, cells were suspended in a solution of recombinant proteins corresponding to the entire FN-L domain (FN-L), Fbg-L domain (Fbg-L), or 1 μM of peptide VIII before the addition to the upper chamber. Migrating cells were fixed and counted under a microscope. Nine high power fields (HPF) were counted for each triplicate. Values shown are from a representative experiment as mean±SEM.

As shown in FIG. 9, Tenascin-C substrate stimulated SMCs chemotaxis compared to BSA, and its level was comparable to the positive control, collagen. In the presence of the Fbg-L domain or peptide VIII, SMCs chemotaxis was inhibited by nearly 70%, whereas the recombinant FN-L domain had no effect. This inhibitory activity is specific, because the Fbg-L domain or peptide VIII did not interfere with the migration of SMCs on collagen substrate. It was therefore concluded that the Fbg-L domain, not the FN-L domain, mediates migration of SMCs on the Tenascin-C substrate, and most likely this occurs through the peptide VIII.

EXAMPLE VII

ANALYSIS OF THE INTERACTION OF SMCS WITH TENASCIN-C

The present invention has identified the factors which control the adhesion of SMCs to Tenascin-C and mapped the active domain as well as the active site of the Tenascin-C molecule. While not necessarily bound by the theory, based on this data, it is proposed that the adhesion & SMCs to Tenascin-C is most likely mediated by integrins, whose mediation is different from that of other cell types. It is different from fibroblasts because heparin sulfate proteoglycan mediates adhesion of fibroblasts to Tenascin-C (21). It is also different from endothelial cells because adhesion of endothelial cells to Tenascin-C is completely blocked by the RGD peptide (20). In contrast, the adhesion of SMCs to Tenascin-C is only partially (30%) blocked by the RGD peptide. This suggests that at least two receptors, one of them RGD-dependent and the other RGD-independent, mediate the adhesion of SMCs to Tenascin-C. Several lines of evidence suggest that these two receptors are most likely integrins, as the adhesion was: 1) completely blocked by EDTA; 2) promoted by $Mg^{2+}$ cation, but not $Ca^{2+}$; 3) completely blocked by the soluble Fbg-L domain or peptide VIII.

The cation-dependent adhesion of SMCs to Tenascin-C may address some of the controversial issues, related to the adhesion of cells to Tenascin-C. Previous studies reported no cell adhesion to Tenascin-C-coated culture dishes (29–32), whereas other reports showed a tweak adhesion of cells (23, 33–37). In accordance with the present invention, adhesion assays were performed with a buffer containing both $Ca^{2+}$ and $Mg^{2+}$. It was observed that increasing $Mg^{2+}$ concentrations increased SMCs adhesion, and maximal adhesion was achieved at 5–10 mM. In addition, the type of cations profoundly affects cell-integrin interaction and in some cases it is a deciding factor whether there is any adhesion at all. For example, the binding activity of $\alpha_2\beta_1$ integrins is promoted by $Mg^{2+}$ cations, and $Ca^{2+}$ reverses the effect of $Mg^{2+}$ (25). This is particularly relevant to adhesion to Tenascin-C, as it has been suggested that $\alpha_2\beta_1$ mediates the interaction of Tenascin-C with endothelial cells (20, 38). Thus, the presence of $Ca^{2+}$ cations in the adhesion buffer may negatively impact adhesion of some cell types to Tenascin-C. Therefore, the concentration of cations and their type may at least partly explain the long controversy about cell-Tenascin-C interaction.

$Mg^{2+}$-mediated modulation may be relevant to the remodeling of the injured arteries after balloon angioplasty. Under normal physiological conditions, the extracellular environment has a higher concentration of $Ca^{2+}$ than $Mg^{2+}$ (39). In contrast, the intracellular $Mg^{2+}$ concentration in a typical mammalian cell is between 15 and 30 mM while intracellular ($Ca^{2+}$ is only about 1–2 μM (40–42). After balloon angioplasty, it is possible that a local increase in extracellular $Mg^{2+}$ levels might occur as the damaged tissue releases its cellular content. It is conceivable that such an increase in the extracellular $Mg^{2+}$ gradient, set up locally from the site of injury, along with growth factors released by the platelets at the injured site, could stimulate Tenascin-C-SMCs interaction possibly through an integrin receptor. This would then provide the stimulus and directional signaling necessary to mobilize SMCs.

The characterization of Tenascin-C isoforms produced by adult and newborn SMCs and the expression of recombinant domains and subdomains allowed mapping of the active domain of Tenascin-C. The present invention has found that the Fbg-L domain accounts for nearly all of the adhesive activity of Tenascin-C and that all the parameters which influence adhesion of SMCs to Tenascin-C also equally affect interaction of SMCs with the Fbg-L domain. As shown by the present invention, experimental artifacts cannot explain the lack of activity of the full-length FN-L domain, and the Fbg-L domain most likely represents an authentic active adhesive domain. This domain is located at the tip of the intact Tenascin-C molecule and is easily accessible for interaction with the cells. The Fbg-L domain is highly conserved among species, and compared to the other domain, it is the most conserved domain of Tenascin-C. Erickson has suggested that other domains may act as a spacer for the Fbg-L domain (43). Since this domain is also involved in SMC migration, it suggests that the initial interaction of SMCs with the Fbg-L domain of Tenascin-C is critical for cell chemotaxis.

In accordance with the present invention, peptide VIII could duplicate nearly all of the activity of the Fbg-L domain when coated onto tissue culture dishes. Since this peptide represents only about 1% of the intact Tenascin-C polypeptide monomer, it suggests that the interaction between the cell surface receptor and this peptide is extremely specific. In addition, peptide VIII is highly conserved. There is a 96% homology between peptide VIII of human and chicken, and the only mutation is the conservative substitution of Arg for Lys, which most likely does not affect the peptide's activity. While not bound by the theory, based on the findings of the present invention, it is hypothesized that this peptide represents the active site of the Fbg-L domain that mediates SMCs adhesion and migration.

Although the timing and location of expression during embryogenesis and its anti-adhesive activity suggest a potential role for Tenascin-C in cell migration, no data directly supporting this idea has been previously reported. The present invention directly shows that Tenascin-C promotes cell migration, and the activity has been mapped to the peptide VIII of the Fbg-L domain. It has been suggested that the migration promoting activity of Tenascin-C may reside on the FN-L domain, specifically the alternatively spliced region, as this region down-regulated focal adhesion points of endothelial cells (44) and SMCs (45). Since down-regulation of focal adhesion points is a prerequisite for migration of adherent cells, it has been suggested that the alternatively spliced region may promote cell migration (44, 45). The present invention found, however, that neither the FN-L domain nor its subdomains inducing the full-length alternatively spliced region had either adhesive or migration promoting activities for detached SMCs, and that the Fbg-L domain can account for nearly all of the activities. However, one may not exclude the possibility that adherent SMCs may need the alternatively spliced region for cell detachment, because the migration assay of the present invention was performed with detached SMCs. It is thus conceivable that the alternatively spliced region is needed to down-regulate focal adhesion points of adherent SMCs and to promote cell detachment. Once detached, however, the Fbg-L domain alone may be sufficient to maintain cell movement.

Tenascin-C is largely expressed during embryonic development, but it is down regulated in adult tissue (19). The present invention found differences in the ability of newborn and adult SMCs to adhere to Tenascin-C, which was consistent throughout multiple isolates and passages of adult and newborn cells. This data suggests that newborn cells have a greater number of stable cell surface receptors for Tenascin-C. In many circumstances, the basic cellular mechanisms that originally were used during embryonic development may be reactivated under pathological conditions. It has been reported that formation of neointima during wound healing in the balloon-injured adult rat carotid artery is dependent on the reexpression of developmentally regulated genes, and the reactivation of these genes may be responsible for the formation of neointima (46–50). The differential ability of the newborn and adult SMCs to adhere to Tenascin-C suggests that the reexpression of a developmentally regulated gene like Tenascin-C provides a suitable substratum for a subpopulation of aortic SMCs to migrate and form neointima.

In summary, the present invention characterizes the parameters that determine the interaction between SMCs and Tenascin-C. The present invention shows that the Fbg-L domain, but not the FN-L domain, is involved in SMCs adhesion and migration. It further mapped the active site of the Fbg-L domain to a 30 amino acid peptide, peptide VIII, which is located near the C-terminal part of the domain. Based on these results, it is hypothesized that the interaction between SMCs and the Fbg-L domain of Tenascin-C is essential for cell adhesion and migration, and blocking this interaction may blunt SMCs migration from media into the neointima and ultimately affect neointimal formation.

The foregoing is meant to illustrate, but not to limit, the scope of the invention. Indeed, those of ordinary skill in the art can readily envision and produce further embodiments, based on the teachings herein, without undue experimentation.

The present invention may be embodied in other specific forms without departing from its essential characteristics. The described embodiment is to be considered in all respects only as illustrative and not as restrictive. The scope of the invention is, therefore, indicated by the appended claims rather than by the foregoing description. All changes which come within the meaning and range of the equivalence of the claims are embraced within the scope of the claims.

SUMMARY OF SEQUENCES

SEQ ID NOs: 1–9 are amino acid sequences of synthetic peptides derived from the Fbg-L domain of the Tenascin-C protein. SEQ ID NO:10 and SEQ ID NO:11 are artificial synthetic peptide sequences.

REFERENCES

1. Jackson et al., *Arterisclerosis and thrombosis*, 13: 1815–1820.
2. Brown et al., *Cardiovascular Res.*, 28: 1815–1820, 1995.
3. Bell and Madri. *Am. J. Pathol.*, 137: 7–2, 1990
4. Clowes, A. W. et al., *LabInvest*, 54: 295–303, 1986.
5. Ferns, G. A. et al., *Atherosclerosis*, 92: 89–104, 1992.
6. Ferns et al., *Science* 253:1129–1132, 1991.
7. Hynes, R. O. et al., *Cell*, 48:549–554, 1989.
8. Lafrenie, R. H. et al., *Cancer Res.*, 52: 2202–2208, 1992.
9. Choi, E. T. et al., *J. Vasc. Surg.*, 19:125–135, 1994
10. Sharifi, B. G., LaFleur, D. W., Pirola, C. J., Forrester, J. S., and Fagin, J. A. (1992) *J. Biol. Chem.*, 267(33), 23910–5
11. LaFleur, D. W., Fagin, J. A., Forrester, J. S., Rubin, S. A., and Sharifi, B. G. (1994) *J. Biol. Chem.*, 269(32), 20757–63
12. Bronner-Fraser, M., Stern, C. D., and Fraser, S (1991) *J. Craniofac. Genet. Dev. Biol.*, 11(4), 214–22
13. Kaplony, A., Zimmermann, D. R., Fischer, R. W., Imhof, B. A., Odermatt, B. F., Winterhalter, K. H., and Vaughan, L. (1991) *Development*, 112(2), 605–14
14. Epperlein, H. H., Halfter, W., and Tucker, R. P. (1988) *Development*, 103(4), 743–56
15. Mackie, E. J., Tucker, R. P., Halfter, W., Chiquet-Ehrismann, R., and Epperlein, H. H. (1988) *Ann. N. Y. Acad. Sci.*, 540, 64–77
16. Spence, S. G., and Poole, T. J. (1994) *Int. J. Dev. Biol.*, 38(1), 85–98
17. Deryugina, E. I., and Bourdon, M. A. (1996) *J. Cell. Sci.*, 109(Pt 3), 643–52
18. Chung, C. Y., Murphy-Ullrich, J. E., and Erickson, H. P. (1996) *Mol. Biol. Cell*, 7(6), 883–92
19. Erickson. H. P., and Bourdon, M. A. (1989) *Annu. Rev. Cell Biol.*, 5, 71–92
20. Joshi, P., Chung, C. Y., Aukhil, I., and Erickson, H. P. (1993) *J. Cell Sci.*, 106(Pt 1), 389–400
21. Aukhil, I., Joshi, P., Yan, Y., and Erickson, H. P. (1993) *J. Biol. Chem.*, 268(4), 2542–53
22. Aufderheide, E., arid Ekblom, P. (1988) *J. Cell Biol.*, 107(6 Pt 1), 2341–9
23. Bourdon, M. A. and Ruoslahti, E. (1989) *J. Cell Biol.*, 108(3), 1149–55
24. Hautanen, A., Gailit, J., Mann, D. M., and Ruoslahti, E. (1989) *J. Biol. Chem.*, 264(3), 1437–42
25. Kirchhofer, D., Languino, L. R., Ruoslahti, E., and Pierschbacher, M. D. (1990) *J. Biol. Chem.*, 265(2), 615–8
26. Smith, J. W., and Cheresh, D. A. (1991) *J. Biol. Chem.*, 266(18), 11429–32
27. Gailit, J., and Ruoslahti, E. (1988) *J. Biol. Chem.*, 263(26), 12927–32
28. Grzesiak, J. J., Davis, G. E., Kirchhofer, D., and Pierschbacher, M. D. (1992) *J. Cell Biol.*, 117(5), 1109–17
29. Lotz, M. M., Burdsal, C. A., Erickson, H. P., and McClay, D. R. (1989) *J. Cell Biol.*, 109(4 Pt 1), 1795–805
30. Lightner, V. A., and Erickson, H. P. (1990) *J. Cell Sci.*, 95(Pt 2), 263–77
31. Aukhil, I., Slemp, C. C., Lightner, V. A., Nishimura, K., Briscoe, G., and Erickson, H. P. (1990) *Matrix* 10(2), 98–111
32. Saginati, M., Siri, A., Balza, E., Ponassi, M., and Zardi, L. (1992) *Eur. J. Biochem.*, 205(2), 545–9
33. Friedlander, D. R., Hoffman, S., and Edelman, G. M. (1988) *J. Cell Biol.*, 107(6 Pt 1), 2329–40
34. Chiquet-Ehrismann, R., Kalla, P., Pearson, C. A., Beck, K., and Chiquet, M. (1988) *Cell*, 53(3), 383–90
35. Spring, J., Beck, K., and Chiquet-Ehrismann, R. (1989) *Cell*, 59(2), 325–34

36. Norenberg, U., Wille, H., Wolff, J. M., Frank, R., and Rathjen, F. G. (1992) *Neuron,* 8(5), 849–63
37. Prieto, A. L., Andersson-Fisone, C., and Crossin, K. L. (1992) *J. Cell Biol.,* 119(3), 663–78
38. Sriramarao, P., Meidler, M., and Bourdon, M. A. (1993) *J. Cell Sci.,* 105(Pt 4), 1001–12
39. Olinger, M. L. (1989) *Emerg. Med. Clin. North Am.,* 7(4), 795–822
40. Polimeni, P. I., and Page, E. (1973) *Circ. Res.,* 33(4), 367–74
41. Henrotte, J. G. (19E8) *Magnesium,* 7(5-6), 306–14
42. Caddell, J. L., and Reed, G. F. (1989) *Magnesium,* 8(2), 65–70
43. Erickson, H. P. (1994) *Perspect Dev. Neurobiol.,* 2(1), 9–19
44. Murphy-Ullrich, J. E., Lightner, V. A., Aukhil, I., Yan, Y. Z., Erickson, H. P., and Hook, M. (1991) *J. Cell Biol.,* 115(4), 1127–36
45. Hahn, A. W., Kern, F., Jonas, U., John, M., Buhler, F. R., and Resink, T. J. (1995) *J. Vasc. Res.,* 32(3), 162–74
46. Majesky, M. W., Giachelli, C. M., Reidy, M. A., and Schwartz, S. M. (1992) *Circ. Res.,* 71(4), 759–68
47. Schwartz, S. M., Reidy, M. R., and Clowes, A. (1985) *Ann. N. Y. Acad. Sci.,* 454, 292–304
48. Schwartz, S. M. (1994) *Exp. Nephrol.,* 2(2), 63–77
49. Schwartz, S. M., Majesky, M. W., and Murry, C. E. (1995) *Atherosclerosis,* 118(Suppl), S125–40
50. Schwartz, S. M., deBlois, D., and E. R, O. B. (1995) *Circ. Res.,* 77(3), 445–65
51. Lemire, J. M., Covin, C. W., White, S., Giachelli, C. M., and Schwartz, S. M. (1994) *Am. J. Pathol.,* 144(5), 1068–81
52. Liaw, L., Almeida, M., Hart, C. E., Schwartz, S. M., and Giachelli, C. M. (1994) *Circ. Res.,* 74(2), 214–24
53. Kirchhofer, D., Grzesiak, J., and Pierschbacher, M. D. (1991) *J. Biol. Chem.,* 266(7), 4471–7

---

What is claimed is:

1. A method of inhibiting the Tenascin-C protein mediated smooth muscle cell adhesion and migration comprising contacting the SMC, smooth muscle cell with an effective amount of a factor capable of reducing the interaction of the SMC with the Tenascin-C protein, wherein the factor is a polypeptide comprising an amino acid sequence selected from the group consisting of SEQ ID NO:3, SEQ ID NO:6, SEQ ID NO:8, and SEQ ID NO:9.

2. The method of claim 1, wherein the polypeptide comprises a Fbg-L, fibrinogen domain of the Tenascin-C protein.

3. The method of claim 1, wherein the polypeptide comprises an amino acid sequence of SEQ ID NO:8.

4. A method of inhibiting Tenascin-C mediated vascular smooth muscle cell adhesion and migration comprising administering to a host in need of the inhibition an effective amount of a factor capable of reducing the interaction of the SMC with the Tenascin-C protein, wherein the factor is a polypeptide comprising an amino acid sequence selected from the group consisting of SEQ ID NO:3, SEQ ID NO:6, SEQ ID NO:8, and SEQ ID NO:9.

5. The method of claim 4, wherein the polypeptide comprises a Fbg-L domain of the Tenascin-C protein.

6. The method of claim 4, wherein the polypeptide comprises an amino acid sequence of SEQ ID NO:8.

7. The method of claim 4, wherein the administration is for treatment of intimal hyperplasia, restenosis, or atherosclerosis.

8. The method of claim 4, wherein the host is human.

* * * * *

UNITED STATES PATENT AND TRADEMARK OFFICE
CERTIFICATE OF CORRECTION

| | | |
|---|---|---|
| PATENT NO. | : 6,124,260 | Page 1 of 1 |
| APPLICATION NO. | : 09/164021 | |
| DATED | : September 26, 2000 | |
| INVENTOR(S) | : Behrooz G. Sharifi and Prediman K. Shah | |

It is certified that error appears in the above-identified patent and that said Letters Patent is hereby corrected as shown below:

Column 1, under the title of the invention, insert the following:

--FEDERAL SUPPORT

This invention was made with U.S. Government support under National Institutes of Health Grant No. HL50566. The U.S. Government may have certain rights in this invention.--

Signed and Sealed this

Tenth Day of February, 2009

JOHN DOLL
*Acting Director of the United States Patent and Trademark Office*